United States Patent
Groves et al.

[11] Patent Number: 6,097,786
[45] Date of Patent: Aug. 1, 2000

[54] METHOD AND APPARATUS FOR MEASURING MULTIPHASE FLOWS

[75] Inventors: Joel Groves, Leonia; Harold Pfutzner, Clarksburg, both of N.J.; Jean-Pierre Poyet, Mamaroneck, N.Y.; Peter Wraight, Skillman, N.J.

[73] Assignee: Schlumberger Technology Corporation, Ridgefield, Conn.

[21] Appl. No.: 09/081,161

[22] Filed: May 18, 1998

[51] Int. Cl.[7] .................................................. G01N 23/06
[52] U.S. Cl. .................................. 378/53; 378/52; 378/54
[58] Field of Search .............................. 250/269.1, 256, 250/358.1; 378/51, 52, 53, 54, 57, 58, 59, 88, 45

[56] References Cited

U.S. PATENT DOCUMENTS

| | | | |
|---|---|---|---|
| 3,435,220 | 3/1969 | Hanken | 378/53 |
| 4,228,353 | 10/1980 | Johnson | 250/356 |
| 4,490,609 | 12/1984 | Chevalier . | |
| 4,562,584 | 12/1985 | Narabayashi | 378/54 |
| 4,788,852 | 12/1988 | Martin et al. . | |
| 5,025,160 | 6/1991 | Watt . | |
| 5,164,590 | 11/1992 | Coles et al. | 250/255 |
| 5,247,559 | 9/1993 | Ohtsuchi et al. | 378/53 |
| 5,689,540 | 11/1997 | Stephenson et al. . | |
| 5,742,660 | 4/1998 | Majewski et al. | 378/98.9 |
| 5,778,041 | 7/1998 | Chase et al. | 378/53 |
| 5,854,820 | 12/1998 | Slijkerman et al. | 378/51 |

FOREIGN PATENT DOCUMENTS

| | | | |
|---|---|---|---|
| 0 236 623 | 9/1987 | European Pat. Off. | G01N 23/06 |
| 59031438 | 2/1984 | Japan | G01N 23/06 |
| 05232007 | 9/1993 | Japan | G01N 9/24 |
| 2 168 150 | 6/1986 | United Kingdom | G01N 9/24 |
| WO 93 24811 | 9/1993 | WIPO . | |
| WO 94 25859 | 10/1994 | WIPO . | |
| WO96/10172 | 4/1996 | WIPO | G01N 23/12 |

OTHER PUBLICATIONS

"Multiphase Flow Measurement Using Multiple Energy Gamma Ray Absorption (MEGRA) Composition Measurement" by A.M. Scheers and W.F.J. Slijkerman. Society of Petroleum Engineers Technical Conference, Oct. 1996.

*Primary Examiner*—David P. Porta
*Attorney, Agent, or Firm*—William B. Batzer; David Garrod

[57] ABSTRACT

A method and apparatus for characterizing a multiphase mixture by irradiating the mixture with X-rays, collecting the photons that emanate from the mixture in response to the irradiation, generating a signal responsive to the aggregate energy of the collected photons, and analyzing the signal to characterize the mixture. Preferably, the mixture is irradiated by repetitively pulsing an X-ray tube and the photons are collected using a multi-layer detector. The method and apparatus may be used to determine the flow rate, flow velocities, and/or composition of the multiphase mixture. In other embodiments, a plurality of X-ray sources and/or detectors may be used.

51 Claims, 8 Drawing Sheets

METHOD AND APPARATUS FOR MEASURING MULTIPHASE FLOWS

FIELD OF THE INVENTION

The present invention relates to multiphase flowmeters, such as those used in the oil industry to estimate fractions and flow rates of oil, water, and gas (i.e., gaseous hydrocarbons, not "gasoline") flowing through pipes. Although the invention is described with reference to its preferred use in oil/gas/water measurements, it is by no means limited to such applications; rather, as will become apparent, aspects of the invention find application in a wide variety of industrial and chemical processes.

BACKGROUND OF THE INVENTION

The capability of measuring the flowrates of multiphase fluids in a pipe-without the need to interrupt fluid flow or separate the phases during the measurement process-has been a long-felt need in the chemical and petroleum industries. Applications of such "multiphase flowmeters" are widespread, particularly in the oil business. Because almost all wells produce a mixture of oil, water, and gas, flow measurements of the individual components of the fluid mixture are essential in the efficient production of a reservoir. Today, at the surface, these measurements are made through separators, which are costly and bulky, especially for offshore applications. The availability of a reliable, cheap, compact, and accurate multiphase meter would satisfy an important and long-felt need in oilfield completion and production operations.

There have been many previous attempts to develop multiphase flowmeters. Generally speaking, these prior-art devices attempt to utilize differences in the absorption of X-rays or Gamma-rays by the oil, water, and gas components of the multiphase mixture. As is well-known by persons skilled in the art, such prior-art devices have limited accuracy, particularly in the case of gas fractions above 90%, a common situation in real-world applications.

Examples of prior-art flowmeters using Gamma-ray sources are disclosed in U.S. Pat. Nos. 4,788,852 and 5,025,160, as well as PCT Publication Nos. WO 93/24811 and WO 94/25859, all of which are incorporated herein by reference. Similarly, examples of X-ray-based devices appear in U.S. Pat. Nos. 4,490,609 and 5,689,540, both of which are also incorporated herein by reference.

One feature shared by all of the aforementioned prior-art devices is the use of spectroscopic analysis of the detected of Gamma-rays and X-rays. Specifically, in each of these systems, there exists a detector which measures the energy of each individual photon received, thus creating a spectrographic picture (or histogram) showing the energy distribution of all received photons. Typically, two independent measurements are obtained by setting a "high energy" window (where the Compton Effect dominates) and a "low energy" window (where the Photoelectric Effect dominates). See '852 patent, claim 1 ("A method of measuring the proportions of various components in a crude oil mixture flowing through a pipeline comprising the steps of . . . detecting the gamma rays or x-rays of at least three distinct energy levels passing through a known volume of the mixture to generate three signals . . . "); '160 patent, col. 2, lines 58–65 ("a method for measuring liquid flow velocity of a multiphase flow containing at least two liquid phases, said method comprising the steps of: . . . (ii) measuring at a first location the intensities of gamma-rays at two different gamma-ray energies, . . ."); '24811 PCT, at 9 ("The signals produced by detector 14 in response to the detected gamma-rays are transmitted to a processing computer unit 16 which determines the intensities of the gamma-rays at both energies"); '25859 PCT, at 4, lines 5–7 ("then, by measuring the radiation absorption through a pipline filled with oil, water and gas, at two gamma-ray energy levels . . ."); '609 patent, col. 2, lines, 37–41 ("By spectral analysis of the resultant flux, two measurements related to respectively the lower and the higher energy ranges are produced, from which . . ."); and '540 patent, col. 2, lines 53–55 ("The detector electronics (not shown) bin the detected energy into histograms as a function of energy."). In order to produce such an energy spectrum from the radiation detector, individual X-ray or Gamma-ray photons received by the detector must be separately analyzed.

SUMMARY OF THE INVENTION

The inventors herein have recognized that the need to process individual photon interactions in the detector of a multiphase flowmeter fundamentally limits the available performance of the flowmeter. Real world applications involve multiphase flow velocity of 10 m/s or greater. Moreover, the flows are highly irregular, especially in situations of high gas concentrations. Thus, in order to accurately characterize such rapid and irregular flows, it is desirable to "capture" the flows over small time intervals (i.e., small enough that the fluid moves negligibly during an interval). For a flow velocity of 10 m/s, the fluid will move 0.01 cm in a 10 $\mu$sec period. Thus, for a spatial resolution of 0.01 cm, the flowmeter must produce a measurement every 10 $\mu$secs.

Currently, the fastest available X-ray or Gamma-ray processing systems can operate with throughputs up to about $10^6$ photons/sec. Therefore, in a 10 $\mu$sec period, while the rapidly moving fluid is approximately constant, only 10 photon interactions in the detector can be processed. However, ten photons is not nearly enough to ensure accuracy in the measurement. (As is well-known among persons skilled in the nuclear arts: to achieve a relative accuracy of 10%, 100 photons are required; and to achieve a relative accuracy of 1%, 10,000 photons are required.) Thus, the inventors herein have concluded that traditional approaches are fundamentally incapable of providing accurate results in real world problems-even using the fastest, most expensive electronics available.

Instead, as the inventors herein have realized, what is desirable to make accurate multiphase flow measurements in a pipe is a means of taking a "flash picture" of the composition of the fluid in the pipe in a time period short relative to the fluid flow fluctuations. In oil production wells, typical fluid flows reach 10 m/sec. If the interrogation region is 1 cm along the direction of fluid flow, then 1% of the fluid will move out of the interrogation region in 10 $\mu$sec. Thus, a 10 $\mu$sec flash (containing a sufficient number of photons) should yield information sufficient to provide instantaneous concentrations of oil, water and gas accurate to the level of 1% within the region probed by the X-ray/detector system. In general, for a three component fluid, two independent measurements must be made during each flash in order to completely characterize the fluid concentrations. The flow rates then can be determined via pressure differential measurements using a Venturi tube or by correlations of "flash" X-ray measurements.

The instant invention eliminates the need to process individual photon interactions during any time period. Rather, only the sum of the radiation collected by (or deposited in) the detectors) during the interrogation interval is measured. As a result, any X-ray flux, however high, can be processed during the chosen time interval.

Accordingly, generally speaking, and without intending to be limiting, one aspect of the invention relates to methods of characterizing a multiphase mixture, such as the following: (i) irradiating said mixture with X-rays; (ii) collecting photons emanating from said mixture in response to said irradiation; (iii) generating a signal responsive to the aggregate energy of the collected photons; and (iv) analyzing the signal to characterize the mixture.

Again, generally speaking, and without intending to be limiting, another aspect of the invention relates to other methods of characterizing a multiphase mixture, such as the following: (i) irradiating said mixture with an X-ray pulse; (ii) collecting energy, including a plurality of photons, emanating from said mixture in response to said X-ray pulse; (iii) generating first and second signals in response to said collected energy; and (iv) analyzing said first and second signals to characterize the mixture.

Again, generally speaking, and without intending to be limiting, another aspect of the invention relates to methods of characterizing a multiphase mixture flowing along a flow path, such as the following: (i) directing a plurality of X-ray photons toward a first location along the flow path of said mixture; (ii) collecting multiple photons of X-rays transmitted through said first location and producing a first signal in response to the collected aggregate energy; (iii) directing a plurality of X-ray photons toward a second location along the flow path of said mixture; (iv) collecting multiple photons of X-rays transmitted through said second location and producing a second signal in response to the collected aggregate energy; and (v) analyzing said first and second signals.

Again, generally speaking, and without intending to be limiting, another aspect of the invention relates to methods of characterizing a multiphase mixture, such as the following: (i) directing a first pulse of X-rays, having a first energy spectrum, into said mixture; (ii) collecting photons emanating from said mixture in response to said first X-ray pulse and generating a first signal in response to the aggregate energy of the photons collected; (iii) directing a second pulse of X-rays, having a second energy spectrum, different from said first spectrum, into said mixture; (iv) collecting photons emanating from said mixture in response to said second X-ray pulse and generating a second signal in response to the aggregate energy of the photons collected; and (v) analyzing the first and second signals to characterize the mixture.

Again, generally speaking, and without intending to be limiting, another aspect of the invention relates to other methods of characterizing a multiphase mixture, such as the following: (i) directing a pulse of X-rays into said mixture; (ii) collecting photons emanating from said mixture in response to said pulse, using a first detector, having a first response characteristic, to produce a first signal, responsive to the aggregate energy of the collected photons; (iii) collecting photons emanating from said mixture in response to said pulse, using a second detector, having a second response characteristic, different from said first response characteristic, to produce a second signal, responsive to the aggregate energy of the collected photons; and, (iv) analyzing the first and second signals to characterize the mixture.

Again, generally speaking, and without intending to be limiting, another aspect of the invention relates to other apparatus for characterizing a multiphase mixture, such as the following combination: (i) an X-ray source irradiating said mixture; (ii) a detector collecting photons emanating from said mixture in response to said irradiation, said detector generating a signal responsive to the aggregate energy of the collected photons; and (iii) means for analyzing the signal to characterize the mixture.

Again, generally speaking, and without intending to be limiting, another aspect of the invention relates to other apparatus for characterizing a multiphase mixture, such as the following combination: (i) a pulsed X-ray source; (ii) a detector, collecting energy, including a plurality of photons, emanating from said mixture in response to said X-ray pulse, and generating first and second signals in response to said collected energy; and (iv) means for analyzing said first and second signals to characterize the mixture.

Again, generally speaking, and without intending to be limiting, another aspect of the invention relates to other apparatus for characterizing a multiphase mixture flowing along a flow path, such as the following combination: (i) an X-ray source, arranged to direct a plurality of X-ray photons toward said mixture; (ii) a first detector, arranged to collect multiple photons of X-rays transmitted through a first location along the flow path of said mixture and produce a first signal in response to the collected aggregate energy; (iii) a second detector, arranged to collect multiple photons of X-rays transmitted through a second location along the flow path of said mixture and produce a second signal in response to the collected aggregate energy; and (iv) means for analyzing said first and second signals.

Again, generally speaking, and without intending to be limiting, another aspect of the invention relates to other apparatus for characterizing a multiphase mixture, such as the following combination: (i) a first X-ray source, generating a first pulse, having a first energy spectrum; (ii) a detector, collecting photons emanating from said mixture in response to said first X-ray pulse and generating a first signal in response to the aggregate energy of the photons collected; (iii) a second X-ray source, generating a second pulse, having a second energy spectrum, different from said first spectrum, said detector collecting photons emanating from said mixture in response to said second X-ray pulse and generating a second signal in response to the aggregate energy of the photons collected; and (iv) means for analyzing the first and second signals to characterize the mixture.

Again, generally speaking, and without intending to be limiting, another aspect of the invention relates to other apparatus for characterizing a multiphase mixture, such as the following combination: (i) a pulsed X-ray source; (ii) a first detector, arranged to collect photons emanating from said mixture in response to said pulse, and having a first response characteristic, so as to produce a first signal, responsive to the aggregate energy of the collected photons; (iii) a second detector, arranged to collect photons emanating from said mixture in response to said pulse, and having a second response characteristic, different from said first response characteristic, so as to produce a second signal, responsive to the aggregate energy of the collected photons; and (iv) means for analyzing the first and second signals to characterize the mixture.

Still other aspects, objects, and advantages of the present invention will become apparent in light of the detailed description below.

BRIEF DESCRIPTION OF THE FIGURES

Selected aspects and/or embodiments of the invention is/are depicted in the attached set of figures, which set is intended to be exemplary (and by no means exhaustive or limiting), and in which.

DESCRIPTION OF THE PREFERRED EMBODIMENTS

Figure 1A:
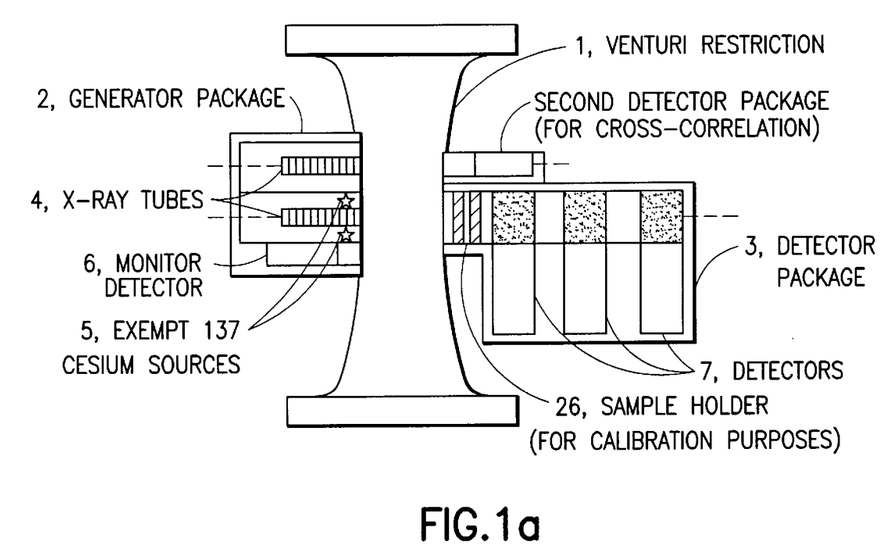
FIG. 1a depicts a first exemplary embodiment of the invention.

Referring to FIG. 1, an exemplary embodiment of the invention illustratively includes a one or more Venturi restrictions (or other pipe(s) or containments)) 1, one or more generator packages 2, and one or more detector packages 3. (As used herein, Venturi means a piece of pipe with a restriction in its middle; this restriction can go to zero, so the term Venturi includes a straight piece of pipe.) A generator package 2 illustratively includes one or more X-ray generator tubes 4, one or more $^{137}$Cs (or other radioactive) sources 5, and one or more monitor detectors 6. X-ray tubes 4 may operate in continuous or pulsed mode. (When more than one tube is used, the additional tube(s) can be used to obtain cross-correlation information—e.g., a second detector package can be installed in front of the second X-ray tube for cross-correlation purposes. Alternatively, such cross-correlation information can be obtained with a single X-ray source and multiple detectors, spatially separated along the direction of the mixture flow.) X-ray tubes can also be multi-headed and operate with successive flashes at different energies.

A monitor detector 6 is preferably located close to the origin of the X-rays. Its function is to measure the X-ray flux, so as to normalize the X-ray output from flash to flash (or to detect and correct possible drifts during continuous mode operation). The X-ray tube itself can be powered either by a continuous power supply (preferably a 60 kV dc supply, as described below) or a pulsed supply. The advantages of the dc power supply are its extremely stable characteristics (especially in terms of voltage) and the fact that it can be run continuously for a period of time, as described below. The pulsed power supply, however, is potentially cheaper and requires less power to operate; it also can lead to a simplification of the detector package.

A Venturi 1 preferably includes a system of collimation and windows transparent to X-rays (in particular, low energy X-rays, around 20 keV) as part of the wall through which the multiphase mixture flows.

Detector package 3 may include a number of detectors 7, each with varying characteristics aimed at capturing selected region(s) of the spectra resulting from the interaction of X-rays with the multiphase mixture. The detector characteristics are optimized so as to maximize the difference between the components of the multiphase mixture. (In the case of an oilfield application, the multiphase mixture is oil, water and gas.) Alternatively, some intermediate detectors can be replaced by filters.

Figure 1B:
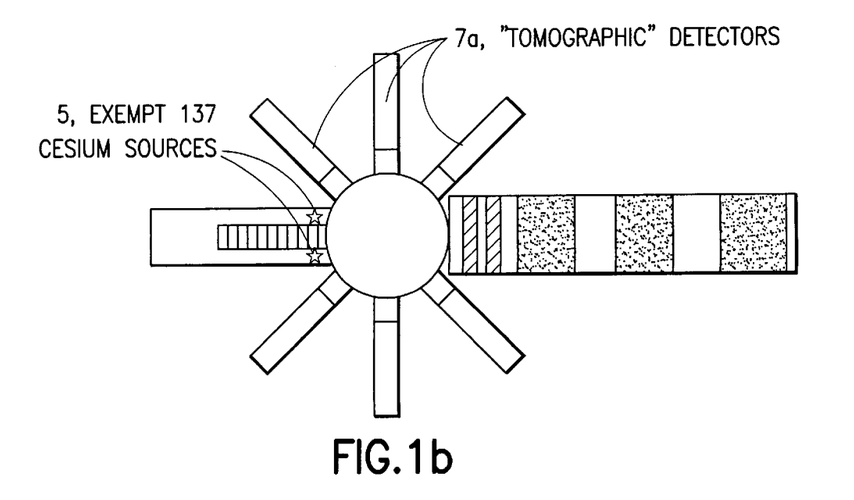
FIG. 1b depicts a top view of the FIG. 1a embodiment.

Referring now to FIG. 1b, a plurality of detectors 7a can be mounted around the pipe and configured to operate in a "tomographic mode"—thereby providing spatial information about the distribution of the multiphase mixture in a cross-section.

The invention preferably involves sending a intense and short flash of X-rays (typically 10 µs or greater) through the multiphase mixture. These X-rays have a characteristic bremsstrahlung spectrum. In traversing the multiphase mixture, the X-rays interact, through various processes, with the mixture, where they are absorbed and scattered. The transmitted X-rays reach a series of detectors, typically mounted on the other side of the pipe and stacked behind each other. A typical detector stack includes a low-energy detector, followed by a detector that stops nearly all the remaining radiation (a "black detector"). Any number of detectors can be used; however, two is a sufficient number for a three-phase mixture, since the three phase fractions must sum to one. (Consequently, two independent pieces of information are used to solve for the three fractions, which are provided by the two (or "dual") detectors.)

The energy absorbed by each detector is a function of the phase fractions. An inversion algorithm is used to extract the phase fractions from the energy absorbed in the detectors.

Figures 2A, 2B:
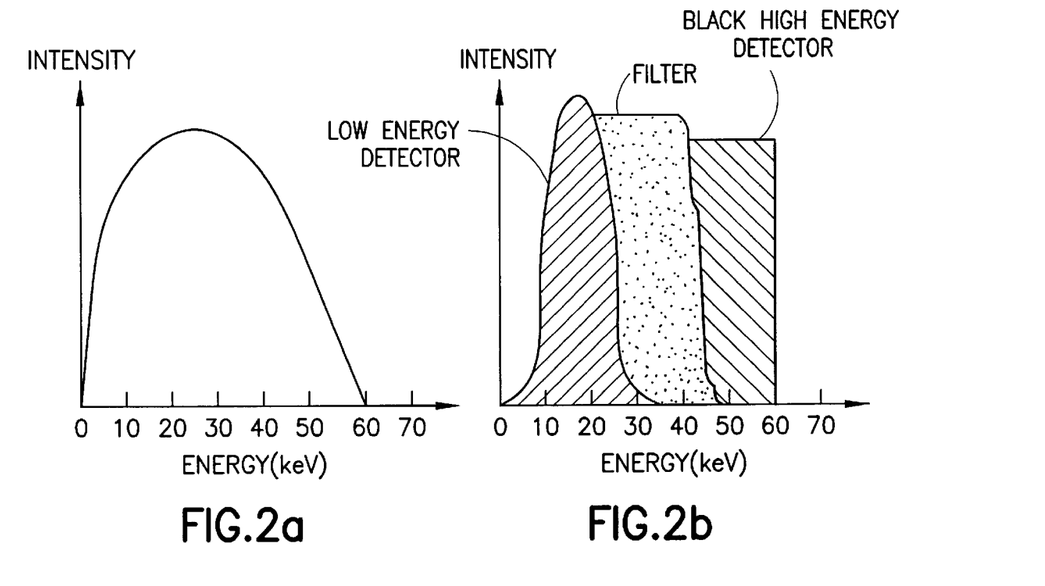
FIG. 2a depicts a typical bremsstrahlung spectrum emitted by an X-ray tube.
FIG. 2b depicts exemplary response functions for a low-energy detector, filter, and high-energy black detector placed successively in the path of an X-ray beam.
Figure 2C:
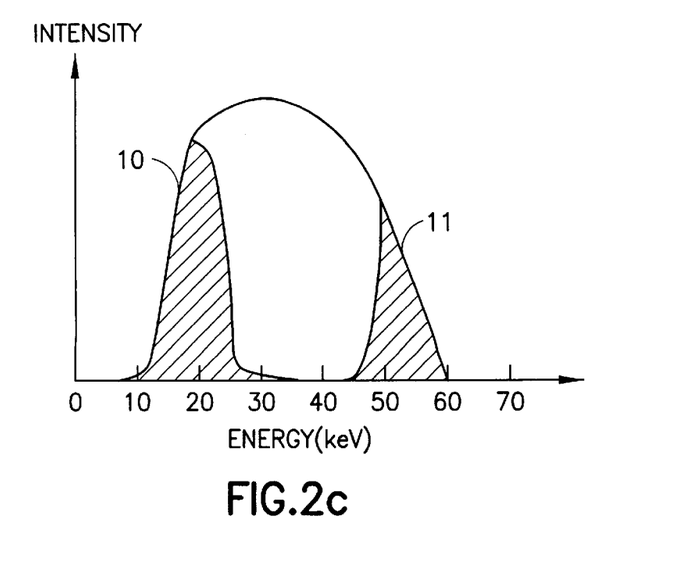
FIG. 2c depicts exemplary energy spectra received by detectors of the type exemplified in FIG. 2b.

In FIG. 2a, an exemplary initial bremsstrahlung spectrum is represented. (NOTE: These, and other, figures herein are intended merely to illustrate and explain concepts related to the invention. Such figures may contain numerical inaccuracies, and may not be drawn to scale.) FIG. 2b shows a typical response sought with the succession of a low energy detector, an intermediate filter, and a black high energy detector. The total energy measured by the low-energy and black detectors is represented as cross-hatched areas 10 and 11 in FIG. 2c, respectively. Each X-ray flash measurement provides a low-energy value (most sensitive to the difference between the oil and water) and a high-energy value (most sensitive to the difference between the liquid and gas).

Such a series of detectors can be advantageously implemented as a set of "sandwiched" semi-conductor materials, each reading part of the output spectrum. This type of implementation offers several advantages—e.g., compactness and easy adaptability to systems in which more than two detectors are used.

Compared to the spectroscopic methods of the prior art, the invention's method of flash X-ray interrogation has the tremendous advantage that it makes full use of the potential power of the X-ray tube. (I.e., whatever the number of photons sent by the tube, only the total energy deposited in each detector is measured; thus, the measurement electronics is only required to handle two such measurements (for a two detector system) per flash.) Consequently, the flash X-ray technique has at least two significant advantages over the prior art. The first is that each "flash" measurement can have a sufficient photon count to minimize nuclear statistics; this is a very significant benefit, since the set of equations needed to derive the final phase fractions is strongly non-linear (in several ways), and, as those skilled in the art will appreciate, can propagate measurement errors in non-intuitive ways, with a strong effect on the final answer. The second advantage is that since the flash measurement can be extremely fast, a high number of flashes can be sent within a short time (typically 100 to 1000 per second) without straining the speed of the associated detector or measurement electronics, but giving an extraordinary detailed "time signature" of the flow, which can be put to good use to improve the final accuracy of the answer.

The invention can also be used to obtain valuable insight into multiphase fluid mechanics. A very sensitive quantity in all the multiphase flowmeters—based on a Venturi principle (Dp measurement between its entrance and its throat)—is the "slip" relationship between the gas and the liquid phases. Traditionally, this relationship (the "slip law") is obtained from measurements in flowloops and tabulated for use under field conditions. However, given the extreme variety of conditions encountered in the field, it will be apparent to persons skilled in the art that laboratory-based slip law predictions will commonly prove inadequate in the field. Accurate slip law information is important, in particular, for a correct prediction of the gas flowrate (or GOR).

In accordance with the instant invention, slip law information can be obtained by leaving the X-ray tube on continuously and by sampling one of the detector channels as fast as possible. (If one samples at 10 μs, 100,000 samples per second can be measured.) One can, then, Fourier transform this signal (or take its power spectrum) to obtain a "signature" of the various structures of the flow—e.g., the difference between large liquid structures, characteristic of the liquid velocity, and small liquid structures, entrained by the gas and characteristic of the gas velocity, can be analyzed. One way to obtain a quantitative estimate of the slip law is to observe how fast the signal changes in one of the detectors while the front of an incoming liquid or gas slug passes by. Information about the length of this front (derived, for example, from existing slug models) gives an approximation of the flow velocity. Alternatively, the size of the X-ray beam can be used (which, in the presently-preferred embodiment, it is on the order of a few millimeters). By sampling fast, for a given large structure, this length, divided by the rise-time of the signal, provides an estimate of the velocity of the structure. Finally, a definitive way to obtain velocity information is to use a second X-ray tube and detector assembly, located downstream (or, alternatively, a single X-ray tube, with multiple, spatially separated detectors), and to cross-correlate the signals from the two detectors.

Exempt Cesium sources (or other radiation sources) find several applications in connection with the invention. First, they are used to stabilize the various detectors in the assembly. A Cesium source, at 662 keV, results in principally Compton interaction. Being exempt, its count rate is low. If one considers that every X-ray flash yields the instantaneous water, oil and gas fractions, then these instantaneous results, when averaged over the time it takes to obtain a reasonable number of counts for the Cesium signal (e.g., 5–10 minutes for typical parameters), should identically verify the averaged time fraction equation for the Cesium. This provides first an intrinsic check of the validity of the X-ray measurement, but can also be used to derive one of the structural parameters of the system: That is, it can be shown that the time averaged fractions can be eliminated from the system to provide a relationship between the attenuation coefficient of the water, oil and gas. As a result, one of these parameters can be derived as a function of the others (such as water salinity). Water salinity can be unambiguously derived because the three pieces of information (low-energy response, high-energy response, and Cesium response) are independent.

X-ray tube(s) used in connection with the invention should preferably deliver a consistent bremsstrahlung spectrum, especially with a stable endpoint voltage. Such X-ray tube(s) also preferably include the capability of pulsing at 100–1000 pulses/second. Those skilled in the art will appreciate that many X-ray tubes fit these preferences. See, e.g., U.S. Pat. No. 5,680,431, X-RAY GENERATOR, by Pietras and Stephenson. The '431 device is particularly preferred because of its ability to be rapidly switched by LEDs and its grounded target.

The nature of a tube's target can be important because it influences the energy makeup of the bremsstrahlung spectrum. An X-ray tube with transmission targets (such as the '431 X-ray tube) is a convenient embodiment. Heavy metal transmission targets (such as gold) should preferably be optimized in thickness so as to limit the reabsorption of photons by the target. One of the preferred tubes is a low Z target (such as Molybdenum), because it produces a fluorescence line within the low-energy window of interest. This packs more low-energy photons in the low-energy window. The matching of such target characteristics to the low-energy detector design significantly improves overall oil and water discrimination.

Figure 3A:
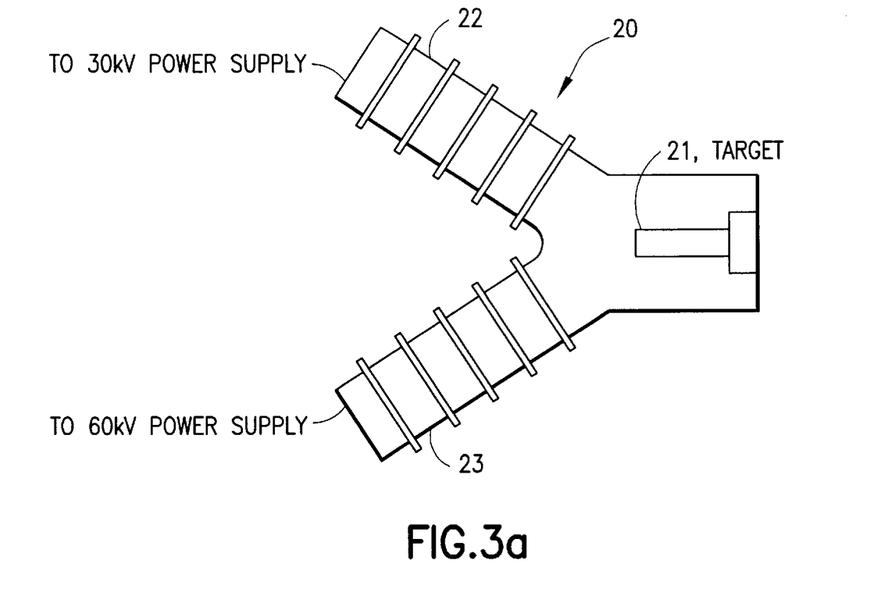
FIG. 3a depicts an exemplary embodiment of a double-headed X-ray tube for use in connection with the invention.

Reference is now made to FIG. 3a, which depicts an exemplary multi-headed (in the illustrated case, two-headed) X-ray tube 20. Tube 20 includes one target 21, but two electron sources 22–23. Such a tube, with two heads, can be operated at two different endpoint energies. Thus, a succession of flashes, alternately at the high energy, then the low energy, can be produced. Using this design, only a single (preferably black) detector 25 is needed in the detector package 24 (see FIG. 3b), because successive high- and low-energy flashes provide the information required to characterize a three-phase mixture.

Exempt Cesium sources used in connection with the invention preferably have a well-defined energy spectrum, which is acquired through a Multichannel Analyzer in the system. This is the only part of the system that requires "spectroscopy." The detector response to X-ray flashes is typically processed through different electronics boards, whose role is just to integrate the light coming from the flash in the detector.

Power supplies used in connection with the invention can be AC or DC. In either case, such supplies should preferably have good endpoint voltage stability.

Low-energy detectors used in connection with the invention should capture the low-energy region of interest (e.g., 10–30 keV) and be as transparent as possible in the high-energy region (e.g., 45–60 keV). Such detectors should also be stable in temperature, given the typical use of multiphase flowmeters in the oilfield. Suitable candidates for such a detector include a plastic scintillator or a transmission ionization chamber, such as a Krypton ionization chamber.

The role of a filter in a dual detector configuration is to reduce the low-energy photon's contribution to the black detector. This results in a notable increase of the dynamic range of the system, especially regarding its ability to handle large (95% and above) gascut situations. In a dual detector implementation, the filter is preferably selected to maximize the dynamic range.

In a dual detector system, the "high energy" detector is the last one and has to capture the leftover radiation. Many candidates can be used, such as NaI, LSO, or CsI. GSO is presently preferred.

Figure 3B:
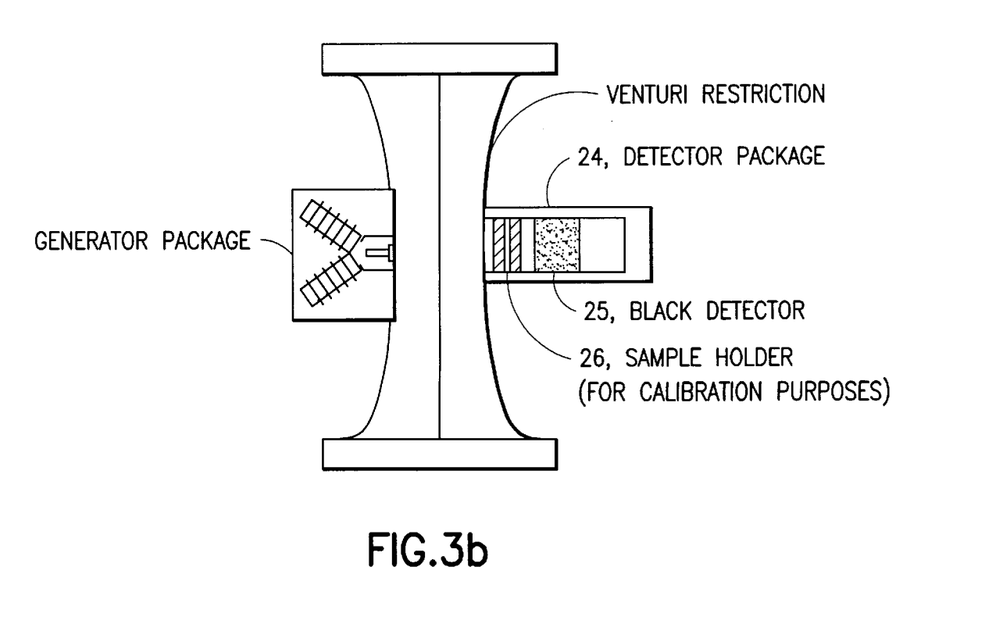
FIG. 3b depicts another exemplary embodiment of the invention.

A sample holder 26 can be used for calibration purposes. It is preferably placed in the path of the X-ray beam, on the detector package side, before the detectors. It can contain, when the pipe is empty, nothing, water, oil, or a known sample or mixture. The response of each detector is then recorded, and this constitutes the calibration of the system for gas, water and oil.

Figure 4:
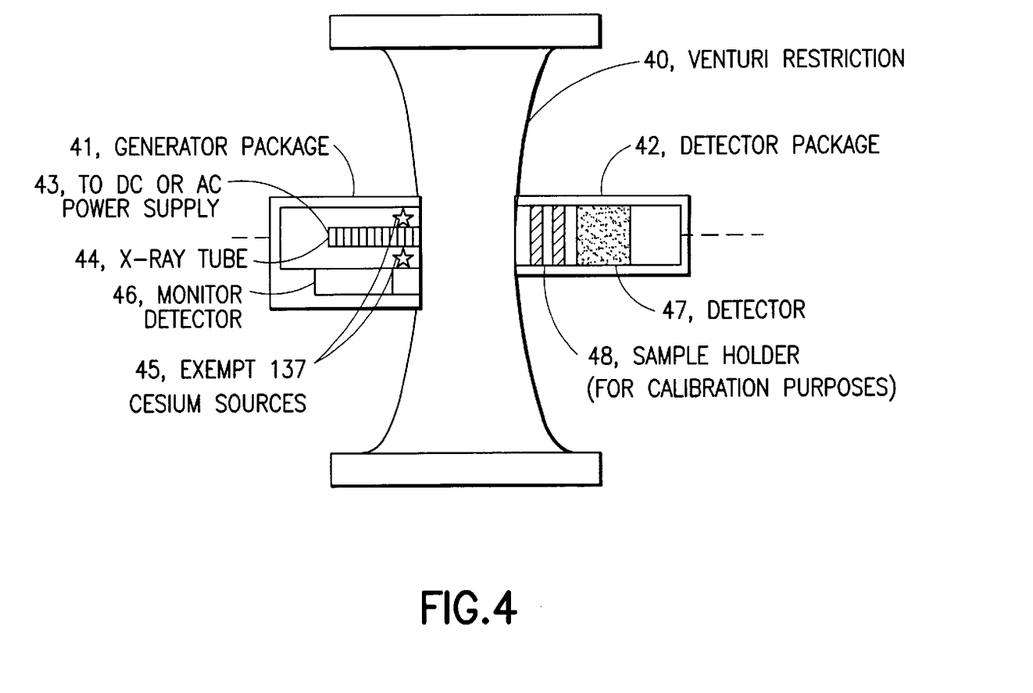
FIG. 4 depicts yet another exemplary embodiment of the invention.

Referring now to FIG. 4, an exemplary embodiment of the invention includes a Venturi 40, generator package 41, and detector package 42.

Generator package 41 preferably includes a DC or AC power supply 43, X-ray tube 44, radiation source 45, and monitor detector 46. X-ray tube 44, preferably powered by a DC power supply, is preferably controlled and pulsed by LEDs and a set of exempt $^{137}$Cs (662 keV) sources 45 in generator package 41.

Detector package 42 includes an X-ray/Gamma-ray detector, oriented toward the throat of Venturi 40. X-rays are generated by the X-ray tube 44 preferably in flashes or bursts, which can be as short as 10 microseconds, or as long as the power supply 45 permits. Gamma-rays are emitted by a radioactive source 45, preferably $^{137}$Cs.

Signal processing electronics (not depicted) differentiates between the weak (e.g., 662 keV) Gamma-rays from the radioactive (e.g., $^{137}$Cs) source and those induced by the X-rays based upon the timing of the X-ray pulse(s). The $^{137}$Cs photons are preferably analyzed through a Multichannel analyzer. For the X-ray photons, only the sum of the X-ray energy deposited in detector 47 during each pulse is analyzed, thus requiring very simple and low-cost electronics with modest speed requirements. A monitor detector 46 is preferably used to normalize fluctuations of the X-ray tube output. The energy requirement for X-ray tube 44 can be very low (e.g., a 30 kV power supply), which contributes to the reliability and the low cost of this embodiment.

Still referring to FIG. 4, the measurements obtained from this system are a set of X-ray flash intensities (there could be, for example, 100 flashes per second, of 10 ms duration each) and a reading of the 662 keV attenuation from the radioactive source(s). The 662 keV data should be acquired for a period of time long enough to minimize nuclear statistical variances.

The system (of FIG. 4) can be operated in several different modes. For example, one can use a pulsed power supply to generate a series of single-energy X-ray pulses, thus obtaining measurements similar to those described above. Using pulsed power allows a low-power system to deliver large instantaneous power during the pulse.

When powering the X-ray tube with a pulsed power supply, it is possible, by pulsing it at different voltages, to retrieve additional information about the flow. For example, a typical use would be to operate the X-ray tube first with a low-energy voltage pulse (30 kV for example), followed, later, by a high-energy pulse (60 kV for example), each individual pulse lasting only a few microseconds. Each pulse will dump a certain quantity of energy into detector 47, thus providing two independent pieces of information (because of the different attenuation mechanisms implicated by each pulse).

In the case of this scheme, where the X-ray tube is pulsed alternately at low (for example, 30 keV) then high (for example, 50 keV) energies, the inventors have made the following striking discovery. For a fixed high-energy endpoint pulse, there exists an optimum low-energy endpoint (the "golden energy") which makes the inversion problem (i.e., the problem of computing phase fraction(s) from the detector signal(s)) linear, to a very good approximation (1% can be reached). This extraordinary result has the effect of simplifying considerably the calibration of the system: At the golden endpoint energy, only a pure water and pure oil calibration is required, without having to know the details of the attenuation of the oil or the water.

The above scheme can be generalized to a set of n (greater than 2) pulses. For example, one could introduce a third, lower-energy pulse (15 or 20 kV for example), to provide additional information about the calibration coefficients of the system. One can also use such information to track possible changes in one of the constituents of the system—e.g., the salinity of the water, the sulfur content of the oil, etc.

Radioactive sources can be used for two very useful purposes. First, they provide an overall quality check, over a few minutes, of the validity of the set of X-ray flashes measured during the same time period. In other words, the average density computed from the fraction derived from the X-ray flashes can be compared, over a given time period, with the measured with the radioactive source. Any drift in the measurement of the X-ray flashes can, therefore, be detected. Second, one can derive three equations for the time-averaged (over the time needed to make one Cesium measurement available) phase fractions (2 from the X-ray flashes, 1 from the Cesium). The sum of the averaged fractions should also be one. Eliminating the phase fraction between these four equations, one is left with an expression linking the calibration coefficients of the oil, water and gas. This equation can be used to calculate one of the calibration parameters: for example, the water salinity or the sulfur content of the oil.

Figure 5:
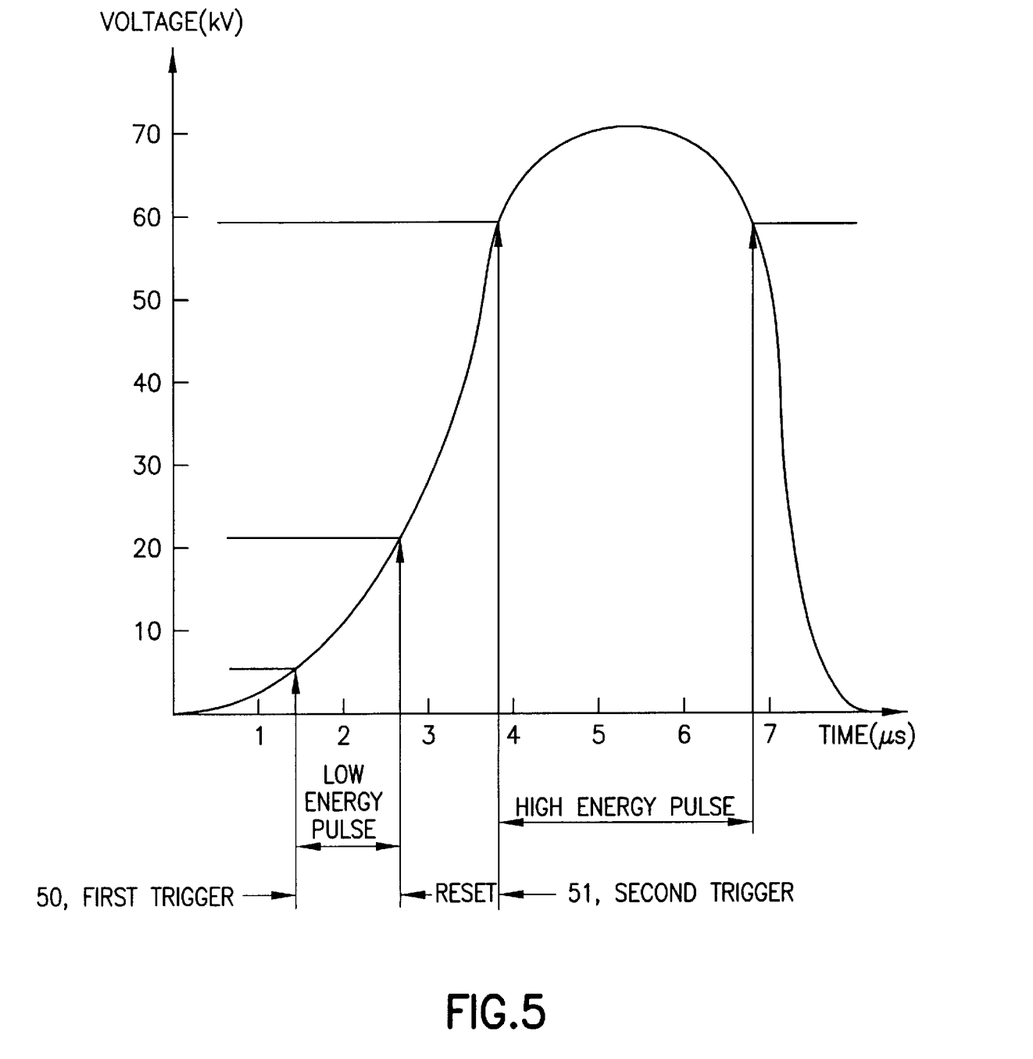
FIG. 5 depicts a triggering technique for use connection with the invention.

Moreover, when using the dual-energy pulsing scheme described above, one can trigger the acquisition electronics according to the voltage of the pulse, as illustrated in FIG. 5. As depicted in FIG. 5, a first trigger 50 provokes an integration during the low-voltage part of the pulse. After a reading of the detector, a second trigger 51 starts the integration (possibly using a second integrator) for the high-voltage part of the pulse. (Note: this technique can be used on the ascending or descending part of the signal). Alternatively, a double-headed (or multi-headed) tube (e.g., FIG. 3a) can be used. Such multi-headed tube(s) can provide a similar flash scheme, alternately flashing between two or more energies, as previously described. Each tube in the multi-headed assembly can also be powered with a DC power supply. This offers the potential advantage of providing a very stable voltage (for a precise measurement) and the ability to deliver arbitrarily long pulses.

Figure 6:
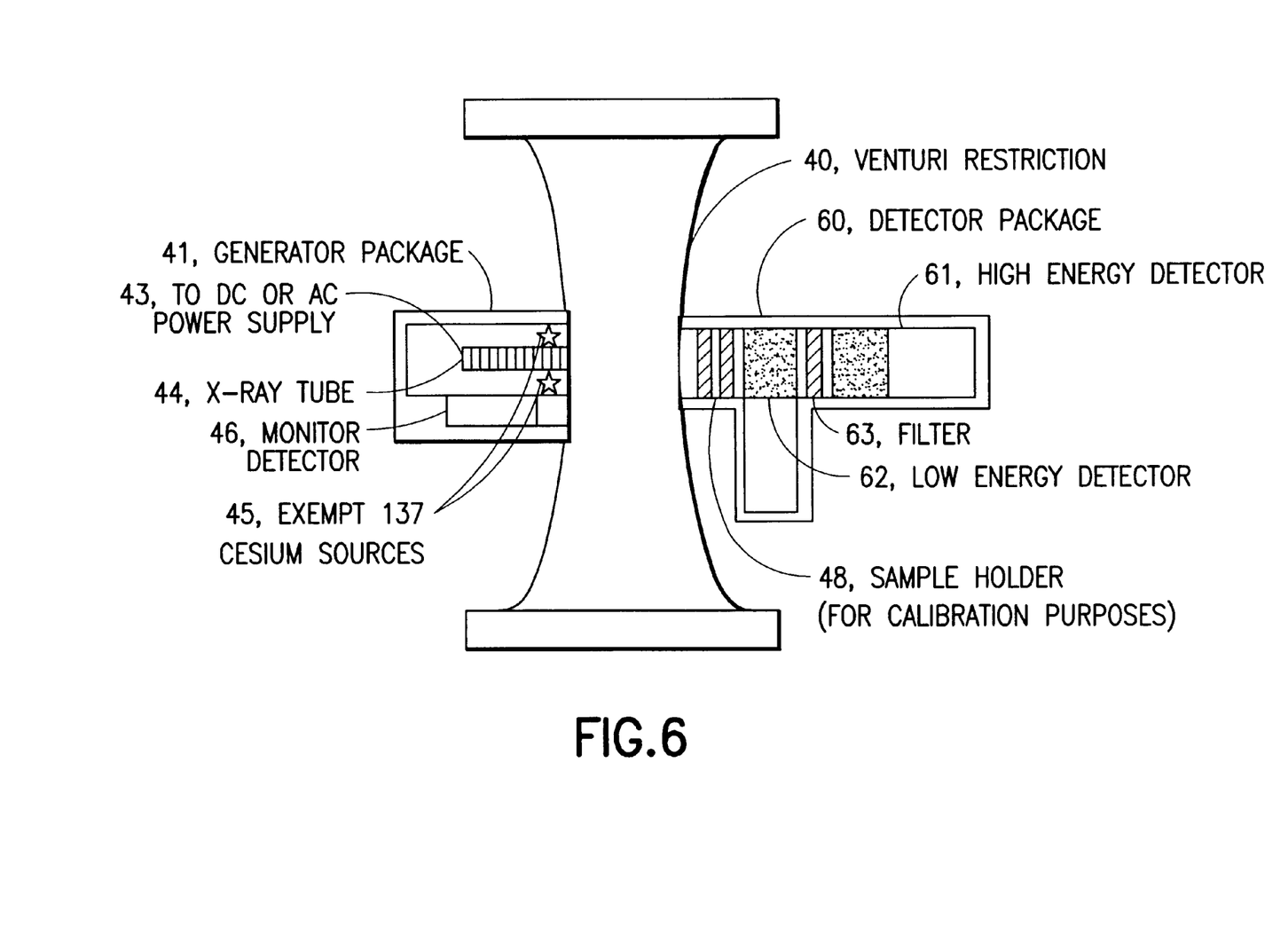
FIG. 6 depicts yet another exemplary embodiment of the invention.

Referring now to FIG. 6, a further exemplary embodiment of the invention includes a detector package 60, containing a high-energy detector 61, filter 63, and low-energy detector 62. Detectors 61 and 62 are designed to be sensitive to different X-ray energies. For example, low-energy detector 61 can be a "thin" detector, capable of primarily stopping X-rays up to 30 keV, and high-energy detector 61 can be a "thick" detector, stopping all the X-rays that reach it. In addition, the presence of a filter 63 between the two detectors, designed to attenuate as much as possible the X-rays below a certain energy, without affecting too much the X-rays to be captured in the high energy windows, increases the difference between the response functions of the two detectors, thus enhancing the dynamic range. Using this embodiment, two pieces of information are obtained per flash. Further information is obtained from a radioactive source 45, as described in connection with the previous embodiment(s).

Generally, in order to make a flowmeter, some velocity information must be derived. This can be done by measuring the pressure differential across the Venturi. This Dp is generally related closely to the liquid velocity (as mentioned earlier, the "slip" between the oil and the water is negligible and they are considered to have the same velocity). Gas velocity is then derived from a "slip law," which is typically calibrated from flowloops. There is no certainty that a given "slip law" will hold for particular multiphase mixtures and conditions in the oilfield. In fact, imprecision in the "slip law" is a well-known problem with conventional flowmeter designs. The invention, because it can sample the multiphase fluid so fast, can calibrate the slip law on site. This is a significant advantage, compared to prior-art approaches.

Using an X-ray tube with a DC power supply, one can leave the tube "on" and sample one of the detector signals as fast as possible with the available electronics (standard electronics should be able to sample at 100 kHz for a short time). The resulting signal contains the time fluctuation of the flow, in particular, different time structures for the gas and liquid events. When large gas slugs pass by the detector, they entrain small liquid structures, which travel almost at the gas velocity. These structures are a signature of the gas velocity. Conversely, when large liquid events occur, one obtains signatures of the liquid velocity. These time signatures can be analyzed in different ways, directly in the time domain or by Fourier transform, or by taking a power spectrum.

A length scale can be introduced in several ways to transform these time signatures into velocities: e.g., the pipe diameter, the size of the collimated X-ray beam, the typical size of a slug front (based on a model), etc. By combining these length estimates with the time signature information, one can derive the slip between the gas and liquid phases.

Alternatively, to estimate these velocities in a direct way, one can cross-correlate the signals from multiple, spatially separated detectors, as exemplified in FIG. 1a. The interpretation of such time signals is similar—i.e., the small liquid drops within large gas events are representative of the gas velocity, while the large liquid slugs give the liquid velocity. The gas/liquid slip velocity is thus measured directly.

As shown in FIG. 1b, an array of detectors around the pipe (a "tomographic detector") can be used to estimate phase concentrations along chords that are not diameters, so as to correct the "line of sight" estimate of the concentrations. Such a "tomographic mode" setup can be used in any of the embodiments described herein.

We will discuss and illustrate below the inversion of the data of the previous system, i.e., how one goes from the measured low and high intensity X-ray signals in the detector(s) to the phase fractions of the multiphase fluid mixture.

The DC power supply case: From a given X-ray flash, one obtains two pieces of data at low and high energy. Let us call the bremstrahlung spectrum f(E). It has an endpoint energy $E_{end}$. The response of the low energy detector can be written:

$$S_L = \int_0^{E_{end}} f(E) e^{-\mu_{window} d_{window}} e^{-(\alpha_o \mu_o + \alpha_w \mu_w + \alpha_g \mu_g)d} (1 - e^{-\mu_L d_L}) dE$$

where:

$S_L$ is the energy deposited in the low energy detector, $\mu_{window}$ is the linear attenuation coefficient of the window material of the walls of the pipe (transparent to X-rays), $d_{window}$ is the total thickness of the wall material (there are two walls), $\alpha_o, \alpha_w, \alpha_g$ are respectively the fraction of oil, water and gas, $\mu_o, \mu_w, \mu_g$ are respectively the oil, water and gas linear attenuation coefficients, d is the internal diameter of the pipe (or Venturi section), $\mu_L$ is the low energy detector linear attenuation coefficient, $d_L$ is the low energy detector thickness.

f(E), $\mu_{window}(E)$, $d_{window}$, $\mu_L(E)$ and $d_L$ are system parameters that are measured in the lab.

$\mu_o(E), \mu_w(E), \mu_g(E)$ are calculated from the known composition of each phase or measured with a high resolution detector.

The sum of the 3 phase fractions is one:

$$\alpha_o + \alpha_w + \alpha_g = 1$$

The signal in the low energy detector can be plotted as a function of the phase fractions or, more physically of the two independent parameters WLR (water/liquid ratio) and GLR (gas liquid ratio).

$$WLR = \frac{\alpha_w}{\alpha_o + \alpha_w}$$

$$GLR = \frac{\alpha_g}{\alpha_o + \alpha_w}$$

Similarly, the response of the high energy detector can be modeled by:

$$S_H = \int_0^{E_{end}} f(E) e^{-\mu_{window} d_{window}} e^{-(\alpha_o \mu_o + \alpha_w \mu_w + \alpha_g \mu_g)d} e^{-\mu_L d_L} e^{-\mu_F d_F} dE$$

where:

$\mu_F$ is the linear attenuation coefficient of the filter, $d_F$ is the thickness of the filter.

$\mu_F(E)$ and dF are system parameters known form the lab.

Figure 7:
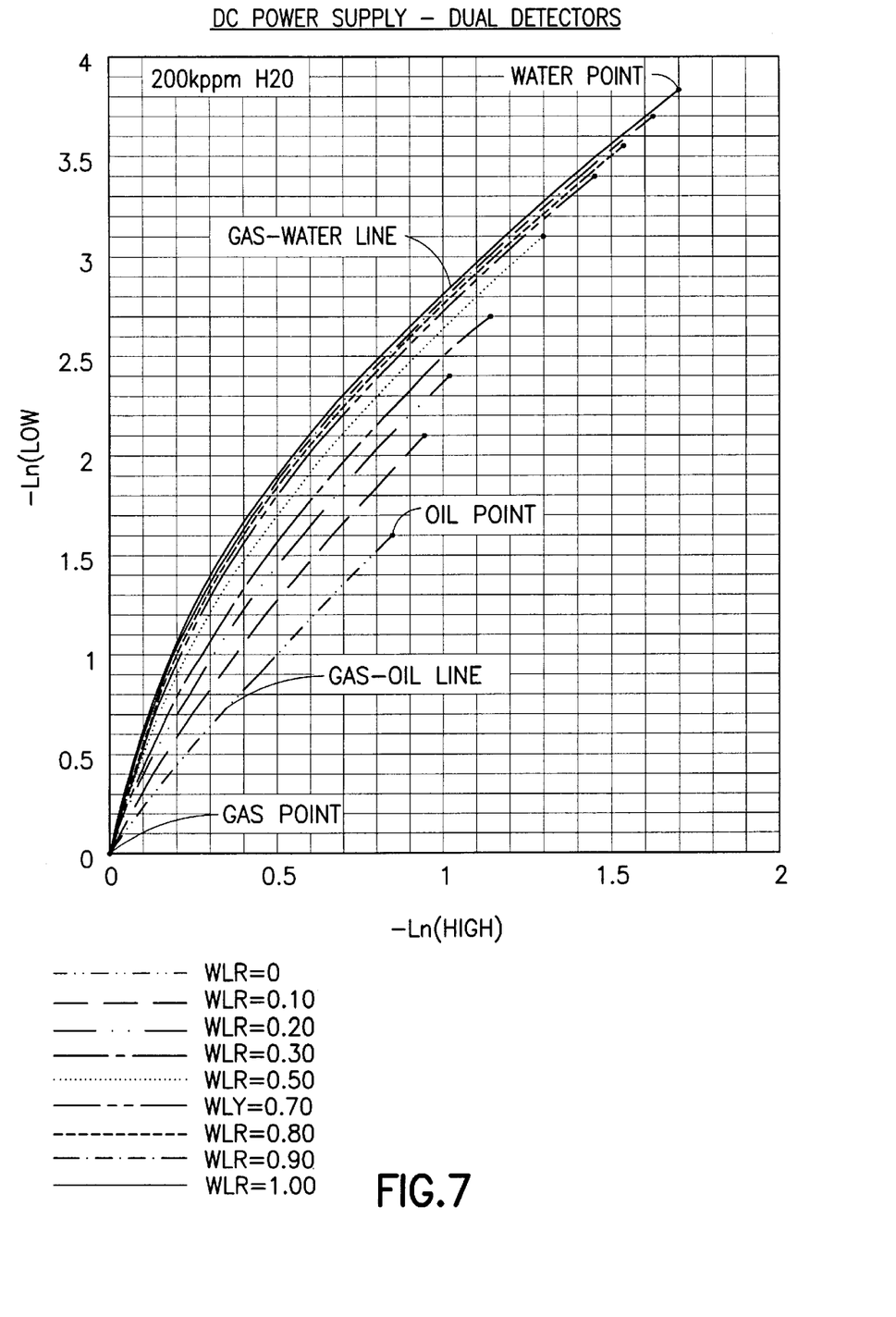
FIGS. 7–8 depict exemplary response functions.

It has been assumed above that the high-energy detector traps all the remaining radiation in the system (i.e., it is black), a very good approximation if one uses GSO as a crystal. The results of this exemplary inversion are summed up in FIG. 7, where the response of the following quantities are plotted:

$$-\ln\left(\frac{S_H}{S_{H_g}}\right) \text{ on the X-axis}$$

$$-\ln\left(\frac{S_L}{S_{L_g}}\right) \text{ on the Y-axis}$$

$S_H$ and $S_L$ are the gas response of the system (so that the gas point is at the origin of the plot).

What appears on FIG. 7 is a curvilinear triangle, whose extremities are the response of the pure phases (gas, oil and water). Once this triangle is tabulated, one can go from the measured parameters ($S_H, S_L$) to the fluid fractions (GLR, WLR) for each X-ray flash.

The AC power supply case: One is now operating at two endpoint energies, $E_L$ and $E_H$ with alternating X-ray flash (or with triggered integrators within the same flash) and a single detection detector. Let us analyze the case of separate flashes (the case of triggered integrators is very similar). The low energy response of the detector is given by:

$$S_L = \int_0^{E_L} f_L(E) e^{-\mu_{window} d_{window}} e^{-(\alpha_o \mu_o + \alpha_w \mu_w + \alpha_g \mu_g)d} e^{-\mu_F d_F} dE$$

where:

$f_L(E)$ is the low energy brehmstrahlung spectrum, measured in the lab.

Similarly, the high energy response is given by:

$$S_H = \int_0^{E_H} f_H(E) e^{-\mu_{window} d_{window}} e^{-(\alpha_o \mu_o + \alpha_w \mu_w + \alpha_g \mu_g)d} e^{-\mu_F d_F} dE$$

where:

$f_H(E)$ is the high energy brehmstrahlung spectrum, measured in the lab.

Figure 8:
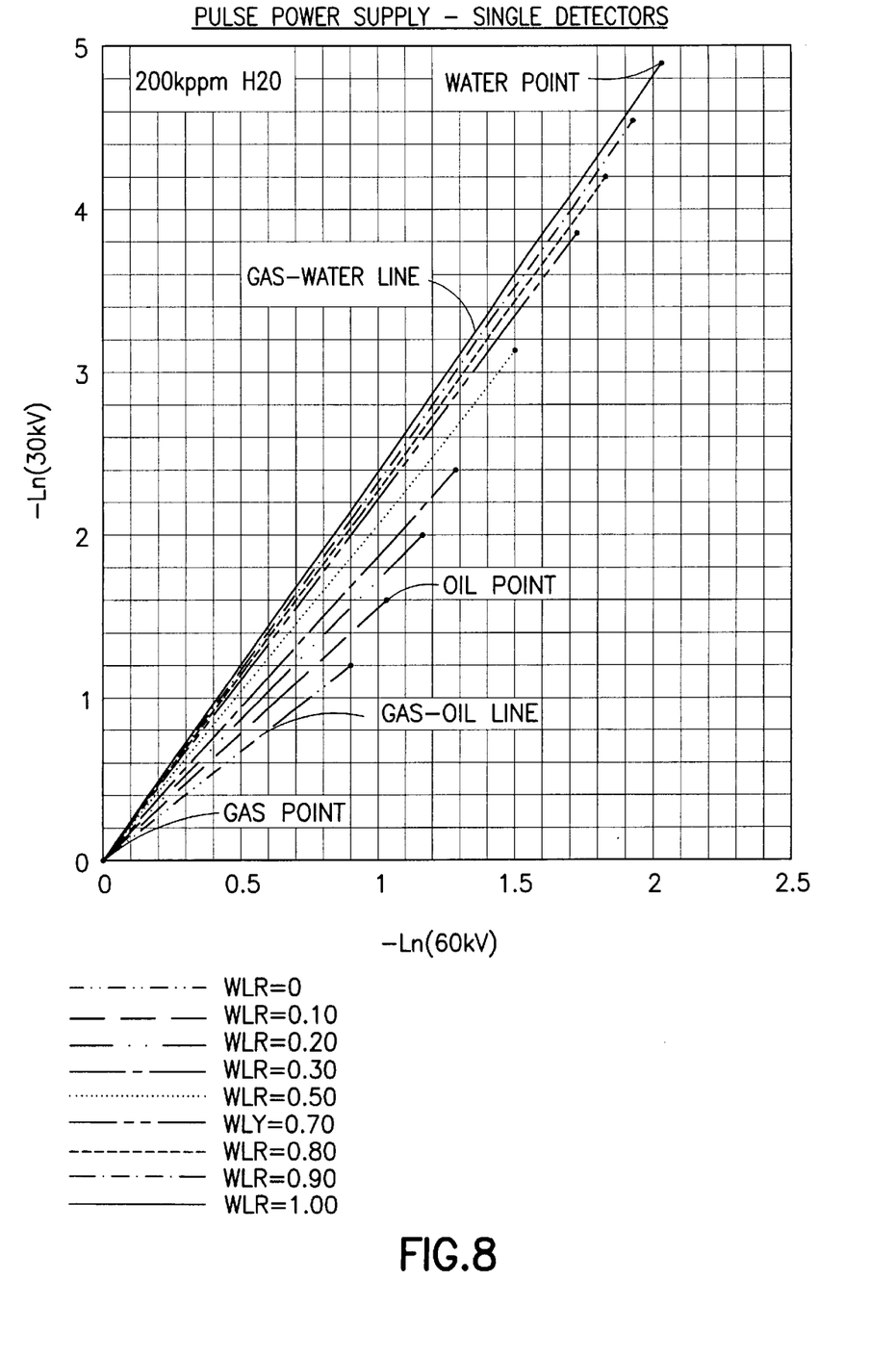

FIG. 8 shows a typical plot of $$-\ln\left(\frac{S_L}{S_{L_g}}\right) \text{ versus } -\ln\left(\frac{S_H}{S_{H_g}}\right).$$

analysis applies as above. However, as can be seen from this plot, the triangle is very close to linearity. This is because we are operating at a low energy of around 30 keV, the so-called "golden energy". This has remarkable consequences for the calibration procedure: Since the inversion is linear, the details of the absorption coefficients versus energy are irrelevant, and the system can be calibrated just by knowing the total response at each corner of the triangle (i.e., for the pure phases) and by linearly interpolating between the corners. If we define:

$$L_w = -\ln\left(\frac{S_{L_w}}{S_{L_g}}\right) \quad H_w = -\ln\left(\frac{S_{H_w}}{S_{H_g}}\right)$$

$$L_o = -\ln\left(\frac{S_{L_o}}{S_{L_g}}\right) \quad H_o = -\ln\left(\frac{S_{H_o}}{S_{H_g}}\right)$$

where these four quantities are obtained from the system when a pure phase is present, we can express the WLR and GLR as:

$$GLR = \frac{(L_w - L_o)(H_w - H) - (H_w - H_o)(L_w - L)}{H(L_w - L_o) - L(H_w - H_o)}$$

$$WLR = \frac{H_o L - L_o H}{L(H_o - H_w) + H(L_w - L_o)}$$

If necessary, this linear approximation can be corrected by the method described previously. The correction can be estimated by linearizing the inversion equations around the estimate of GLR and WLR above.

While the foregoing has described and exemplified aspects of various embodiments of the present invention, those skilled in the art will recognize that alternative elements and techniques, and/or combinations and permutations of the described elements and techniques, can be substituted for, or added to, the embodiments and methods described herein.

What is claimed is:

1. A method of characterizing a multiphase mixture, comprising the following acts:

(i) irradiating said mixture with X-rays;

(ii) collecting photons emanating from said mixture in response to said irradiation;

(iii) generating a signal responsive to the aggregate energy of the collected photons; and, (iv) analyzing the signal to characterize the mixture, said act (iv) comprising computing flow velocities for one or more component(s) of the mixture.

2. A method of characterizing a multiphase mixture, as defined in claim 1, wherein act (i) comprises pulsing an X-ray tube.

3. A method of characterizing a multiphase mixture, as defined in claim 1, wherein act (i) comprises repetitively pulsing an X-ray tube.

4. A method of characterizing a multiphase mixture, as defined in claim 1, wherein act (i) comprises alternately pulsing an X-ray tube with first and second voltages.

5. A method of characterizing a multiphase mixture, as defined in claim 1, wherein act (i) comprises alternately pulsing a multi-headed X-ray tube.

6. A method of characterizing a multiphase mixture, as defined in claim 1, wherein act (i) comprises continuously producing X-rays using a DC-powered X-ray tube.

7. A method of characterizing a multiphase mixture, as defined in claim 1, wherein act (i) comprises irradiating said mixture with X-rays from a plurality of X-ray sources surrounding the mixture.

8. A method of characterizing a multiphase mixture, as defined in claim 1, wherein act (ii) comprises collecting photons in a black detector.

9. A method of characterizing a multiphase mixture, as defined in claim 1, wherein act (ii) comprises collecting photons with a detector having a defined response function.

10. A method of characterizing a multiphase mixture, as defined in claim 1, wherein act (ii) comprises directing photons into a filter and collecting those photons which pass through the filter in a black detector.

11. A method of characterizing a multiphase mixture, as defined in claim 1, wherein act (ii) comprises collecting photons deposited in a stage of a multi-layer detector.

12. A method of characterizing a multiphase mixture, as defined in claim 1, wherein act (ii) comprises collecting photons in a plurality of detectors surrounding the mixture.

13. A method of characterizing a multiphase mixture, as defined in claim 1, wherein act (iii) comprises triggering a detector to create a signal responsive to the aggregate energy of photons collected by the detector.

14. A method of characterizing a multiphase mixture, as defined in claim 1, wherein act (iii) comprises periodically triggering a detector to create a signal responsive to the aggregate energy of photons collected by the detector.

15. A method of characterizing a multiphase mixture, as defined in claim 1, wherein act (iii) comprises triggering a detector periodically, and in harmony with the triggering of an X-ray source, to create a signal responsive to the aggregate energy of photons collected by the detector.

16. A method of characterizing a multiphase mixture, as defined in claim 15, wherein act (ii) further comprises setting a relative trigger delay, between source and detector, to selectively collect photons within a preferred energy spectrum.

17. A method of characterizing a multiphase mixture, as defined in claim 1, wherein act (iv) comprises detecting components of the mixture.

18. A method of characterizing a multiphase mixture, as defined in claim 1, wherein act (iv) comprises detecting the passage of slugs flowing in the mixture.

19. Apparatus for characterizing a multiphase mixture, comprising:

(i) a first X-ray source, generating a first pulse, having a first energy spectrum;

(ii) a detector, collecting photons emanating from said mixture in response to said first X-ray pulse and generating a first signal in response to the aggregate energy of the photons collected;

(iii) a second X-ray source, generating a second pulse, having a second energy spectrum, different from said first spectrum, said detector collecting photons emanating from said mixture in response to said second X-ray pulse and generating a second signal in response to the aggregate energy of the photons collected; and, (iv) means for analyzing the first and second signals to characterize the mixture.

20. A method of characterizing a multiphase mixture, comprising the following acts:

(i) irradiating said mixture with an X-ray pulse;

(ii) collecting energy in a multi-layer detector, including a plurality of photons, emanating from said mixture in response to said X-ray pulse;

(iii) generating first and second signals in response to said collected energy; and, (iv) analyzing said first and second signals to characterize the mixture.

21. A method of characterizing a multiphase mixture, as defined in claim 20, wherein act (iii) comprises generating said first signal from energy collected in a first stage of a multi-layer detector, and generating said second signal from energy collected in a second stage of said multi-layer detector.

22. Apparatus for characterizing a multiphase mixture, comprising:

(i) a pulsed X-ray source;

(ii) a first detector, arranged to collect photons emanating from said mixture in response to said pulse, and having a first response characteristic, so as to produce a first signal, responsive to the aggregate energy of the collected photons;

(iii) a second detector, arranged to collect photons emanating from said mixture in response to said pulse, and having a second response characteristic, different from said first response characteristic, so as to produce a second signal, responsive to the aggregate energy of the collected photons; and, (iv) means for analyzing the first and second signals to characterize the mixture.

23. A method of characterizing a multiphase mixture flowing along a flow path, comprising the following acts:

(i) directing a plurality of X-ray photons toward a first location along the flow path of said mixture;

(ii) collecting multiple photons of X-rays transmitted through said first location and producing a first signal in response to the collected aggregate energy;

(iii) directing a plurality of X-ray photons toward a second location along the flow path of said mixture;

(iv) collecting multiple photons of X-rays transmitted through said second location and producing a second signal in response to the collected aggregate energy; and, (v) analyzing said first and second signals.

24. A method of characterizing a multiphase mixture, as defined in claim 23, wherein act (v) includes determining the flow rate of the mixture along the flow path.

25. A method of characterizing a multiphase mixture, as defined in claim 23, wherein act (v) includes cross-correlating said first and second signals.

26. A method of characterizing a multiphase mixture, as defined in claim 23, wherein act (v) includes determining the flow velocities for individual components of the mixture.

27. A method of characterizing a multiphase mixture, as defined in claim 23, wherein act (v) includes determining the composition of the mixture.

28. A method of characterizing a multiphase mixture, comprising the following acts:

(i) directing a pulse of X-rays into said mixture;

(ii) collecting photons emanating from said mixture in response to said pulse, using a first detector, having a first response characteristic, to produce a first signal, responsive to the aggregate energy of the collected photons;

(iii) collecting photons emanating from said mixture in response to said pulse, using a second detector, having a second response characteristic, different from said first response characteristic, to produce a second signal, responsive to the aggregate energy of the collected photons; and, (iv) analyzing the first and second signals to characterize the mixture.

29. Apparatus for characterizing a multiphase mixture, comprising:

(i) an X-ray source irradiating such mixture;

(ii) a detector collecting photons emanating from said mixture in response to said irradiation, said detector generating a signal responsive to the aggregate energy of the collected photons; and (iii) means for analyzing the signal to characterize the mixture, said means for analyzing computing flow velocities for one or more component(s) of the mixture.

30. Apparatus for characterizing a multiphase mixture, as defined in claim 29, wherein said means for analyzing detects the passage of slugs flowing in the mixture.

31. Apparatus for characterizing a multiphase mixture, as defined in claim 29, wherein (i) comprises a pulsed X-ray tube.

32. Apparatus for characterizing a multiphase mixture, as defined in claim 29, wherein (i) comprises a pulsed X-ray tube having first and second voltage sources.

33. Apparatus for characterizing a multiphase mixture, as defined in claim 29, wherein (i) comprises a multi-headed X-ray tube.

34. Apparatus for characterizing a multiphase mixture, as defined in claim 29, wherein (i) comprises a continuous DC-powered X-ray tube.

35. Apparatus for characterizing a multiphase mixture, as defined in claim 29, wherein (i) comprises a plurality of X-ray sources surrounding the mixture.

36. Apparatus for characterizing a multiphase mixture, as defined in claim 29, wherein said detector is a black detector.

37. Apparatus for characterizing a multiphase mixture, as defined in claim 29, wherein said detector has a defined response function.

38. Apparatus for characterizing a multiphase mixture, as defined in claim 29, wherein said detector comprises a filter, followed by a black detector.

39. Apparatus for characterizing a multiphase mixture, as defined in claim 29, wherein said detector comprises a stage of a multi-layer detector.

40. Apparatus for characterizing a multiphase mixture, as defined in claim 29, wherein said detector comprises a plurality of detectors surrounding the mixture.

41. Apparatus for characterizing a multiphase mixture, as defined in claim 29, further including means for providing a relative trigger delay between said source and detector.

42. Apparatus for characterizing a multiphase mixture, as defined in claim 29, further comprising means for setting a relative trigger delay, between source and detector, to selectively collect photons within a preferred energy spectrum.

43. Apparatus for characterizing a multiphase mixture, as defined in claim 29, wherein said means for analyzing detects components of the mixture.

44. Apparatus for characterizing a multiphase mixture, comprising:
  (i) a pulsed X-ray source;
  (ii) a detector, collecting energy, including a plurality of photons, emanating from said mixture in response to said X-ray pulse, and generating first and second signals in response to said collected energy; and,
  (iv) means for analyzing said first and second signals to characterize the mixture.

45. Apparatus for characterizing a multiphase mixture, as defined in claim 44, wherein said detector comprises a multi-layer detector.

46. Apparatus for characterizing a multiphase mixture, as defined in claim 45, wherein a first stage of said multi-layer detector generates said first signal, and a second stage of said multi-layer detector generates said second signal.

47. Apparatus for characterizing a multiphase mixture flowing along a flow path, comprising:
  (i) an X-ray source, arranged to direct a plurality of X-ray photons toward said mixture;
  (ii) a first detector, arranged to collect multiple photons of X-rays transmitted through a first location along the flow path of said mixture and produce a first signal in response to the collected aggregate energy;
  (iii) a second detector, arranged to collect multiple photons of X-rays transmitted through a second location along the flow path of said mixture and produce a second signal in response to the collected aggregate energy; and,
  (iv) means for analyzing said first and second signals.

48. Apparatus for characterizing a multiphase mixture, as defined in claim 47, wherein said means for analyzing determines the flow rate of the mixture along the flow path.

49. Apparatus for characterizing a multiphase mixture, as defined in claim 47, wherein said means for analyzing cross-correlates said first and second signals.

50. Apparatus for characterizing a multiphase mixture, as defined in claim 47, wherein said means for analyzing determines the flow velocities for individual components of the mixture.

51. Apparatus for characterizing a multiphase mixture, as defined in claim 47, wherein said means for analyzing determines the composition of the mixture.

* * * * *